US012184957B2

United States Patent
Hale

(10) Patent No.: US 12,184,957 B2
(45) Date of Patent: Dec. 31, 2024

(54) ELECTRICAL DEVICE WITH A SINGLE INTERFACE FOR ACCOMMODATING MULTIPLE CONNECTOR TYPES, AND A CONNECTOR KIT

(71) Applicant: KARL STORZ Imaging, Inc., Goleta, CA (US)

(72) Inventor: Eric L Hale, Vancouver, WA (US)

(73) Assignee: KARL STORZ Imaging, Inc., Goleta, CA (US)

(*) Notice: Subject to any disclaimer, the term of this patent is extended or adjusted under 35 U.S.C. 154(b) by 468 days.

(21) Appl. No.: 17/645,238

(22) Filed: Dec. 20, 2021

(65) Prior Publication Data
US 2023/0199283 A1 Jun. 22, 2023

(51) Int. Cl.
| | | |
|---|---|---|
| *H04N 23/50* | (2023.01) | |
| *A61B 1/045* | (2006.01) | |
| *H01R 13/659* | (2011.01) | |
| *H01R 27/02* | (2006.01) | |
| *H04N 23/65* | (2023.01) | |
| *H04N 23/66* | (2023.01) | |

(52) U.S. Cl.
CPC ........... *H04N 23/50* (2023.01); *H01R 13/659* (2013.01); *H01R 27/02* (2013.01); *H04N 23/65* (2023.01); *H04N 23/66* (2023.01); *A61B 1/045* (2013.01); *H04N 23/555* (2023.01)

(58) Field of Classification Search
CPC .................................................. H01R 13/659
See application file for complete search history.

(56) References Cited

U.S. PATENT DOCUMENTS

| | | | | |
|---|---|---|---|---|
| 6,184,922 B1 * | 2/2001 | Saito | ...................... | H04N 19/61 |
| | | | | 600/109 |
| 6,469,901 B1 | 10/2002 | Costner | | |
| 7,841,776 B2 * | 11/2010 | DiFonzo | ................ | H01R 24/00 |
| | | | | 385/74 |

(Continued)

FOREIGN PATENT DOCUMENTS

| | | |
|---|---|---|
| WO | 0227465 A1 | 4/2002 |
| WO | 2014139699 A1 | 9/2014 |

OTHER PUBLICATIONS

Albert, J., European Search Report, Apr. 25, 2023, pp. 1-7, European Patent Office, Munich.

*Primary Examiner* — Abdullah A Riyami
*Assistant Examiner* — Amara Anderson
(74) *Attorney, Agent, or Firm* — David N. Villalpando; Jacqueline Cohen

(57) ABSTRACT

An electrical device and a video camera system for transmitting and receiving data to at least one auxiliary device is provided. The electrical device includes electrical components for receiving, transmitting and processing the data. The electrical components are further configured to transmit power. The electrical device includes a housing for accommodating the electrical components. An interface is disposed on the housing. The interface includes a plurality of data ports, a first power port and a second power port. The plurality of data ports is disposed between the first power port and the second power port. The interface is configured to mate with a plurality of connectors, each of which are coupled to the auxiliary device so as to power the respective auxiliary device and transmit and receive data to and from the auxiliary device.

18 Claims, 9 Drawing Sheets

(56) References Cited

U.S. PATENT DOCUMENTS

| | | |
|---|---|---|
| 9,106,031 B2 | 8/2015 | Golko |
| 2011/0294348 A1 | 12/2011 | McAlonis |
| 2012/0014384 A1 | 1/2012 | Diab |
| 2016/0128549 A1* | 5/2016 | Juergens ................ A61B 1/045 |
| | | 600/112 |
| 2016/0261063 A1 | 9/2016 | Flender |
| 2017/0172400 A1* | 6/2017 | Shimomura ....... A61B 1/00126 |
| 2017/0336579 A1 | 11/2017 | Sanandajifar et al. |
| 2020/0078110 A1* | 3/2020 | Henderson .............. H04L 67/10 |
| 2020/0187758 A1* | 6/2020 | Duckett, III ....... A61B 1/00114 |
| 2021/0173947 A1* | 6/2021 | Li ...................... G06F 12/0891 |

* cited by examiner

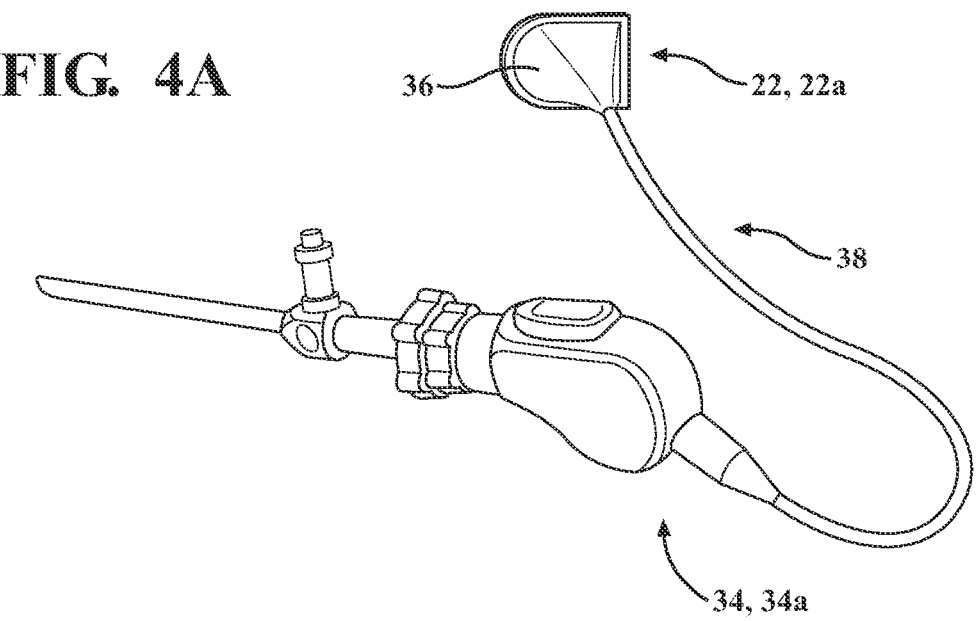
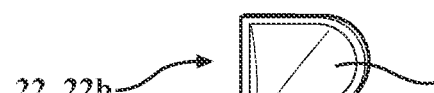
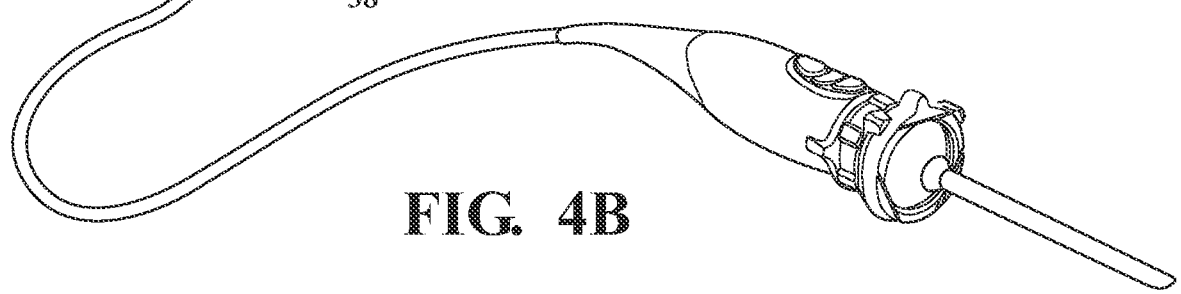

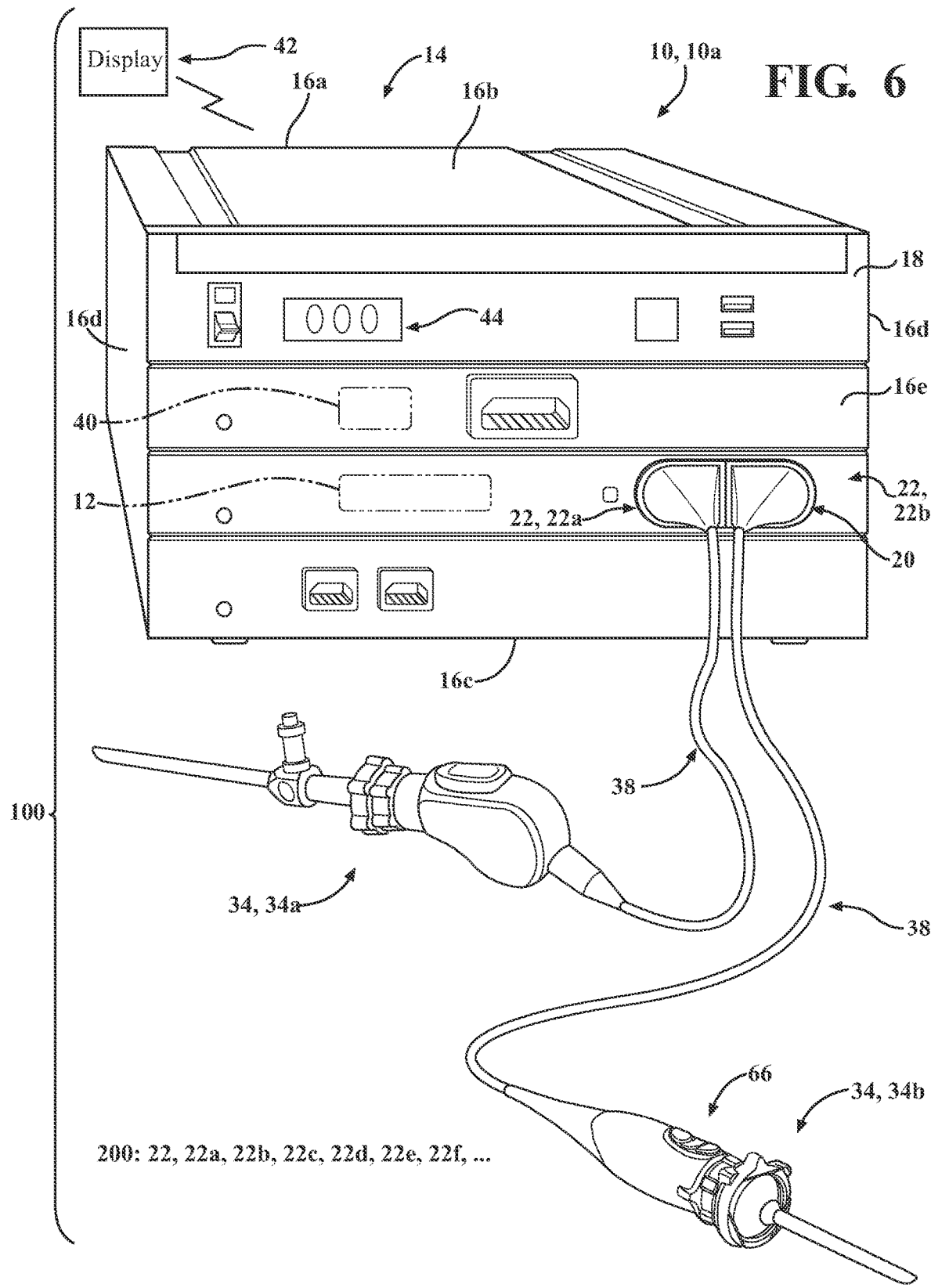

ELECTRICAL DEVICE WITH A SINGLE INTERFACE FOR ACCOMMODATING MULTIPLE CONNECTOR TYPES, AND A CONNECTOR KIT

The present disclosure relates generally to the field of an electrical device and a connector kit for use with the electrical device.

BACKGROUND

An electrical device 500 may be configured to power auxiliary devices 600*a*, 600*b* as well as process data from the auxiliary devices 600*a*, 600*b*. An exemplary device, such as a camera controller, includes an interface 502 configured to attach to a connector 602. The connector 602 is electrically coupled to the auxiliary device 600*a*, 600*b*, such as a camera head or a videoscope. Currently, electrical devices 500 include a plurality of interfaces 502, each configured to connect to a specific auxiliary device so as to power the electrical device 502 as well as receive data from the auxiliary device 600*a*, 600*b*. The connectors 602 may be the same or may be different and may include standard connectors, such as a standard HDMI connector, micro HDMI connector or the like, or proprietary connectors.

An example of an electric device 500 is shown in FIGS. 1 and 2. For illustrative purposes, the electrical device 500 is shown as a camera controller. The electric device 500 includes the pair of interfaces 502, each interface configured to receive the auxiliary device 600*a*, 600*b*. This requires additional circuits and wiring which increases the packing space requirements.

Accordingly, it remains desirable to have an electrical device with a single interface configured to receive more than one type of connector and multiple connectors from multiple auxiliary devices so as to reduce the packaging space, and accommodate different connectors.

SUMMARY

In one aspect of the disclosure, an electrical device for transmitting and receiving data is provided. The electrical device includes electrical components for receiving, transmitting and processing data. The electrical components are further configured to transmit power. The electrical device includes a housing for accommodating the electrical components.

The housing includes a panel. The panel includes an interface. The interface includes a plurality of data ports, a first power port and a second power port. The plurality of data ports is disposed between the first power port and the second power port. The interface is configured to mate with a plurality of connectors, each of which are coupled to an auxiliary device so as to power the respective auxiliary device and transmit and receive data to and from the auxiliary device.

In one aspect of the electrical device, the plurality of data ports includes a first series of data ports and a second series of data ports. The first series of data ports includes a first predetermined number of data ports and the second series of data ports includes a second predetermined number of data ports. The data ports of the first series of data ports are arranged along a common axis. Likewise, the data ports of the second series of data ports are arranged along a common axis.

In another aspect of the electrical device, the first power port and the second power port are configured to transmit power wirelessly. In such an aspect, the plurality of data ports may be configured to transmit the data wirelessly.

In another aspect of the electrical device, the electrical device further includes a first pair of alignment members and a second pair of alignment members. In such an aspect, one of the first pair of alignment members is centered within the first power port and one of the second pair of alignment members is centered within the second power port.

In yet another aspect of the electrical device, the first series of data ports includes a first uplink port configured to transmit data and the second series of data ports includes a second uplink port configured to transmit data. For example, the data is transmitted from the electrical device to the attached auxiliary device to execute a programmed function. In such an aspect, the first uplink port is the first data port in the first series of data ports and the second uplink port is the last data port in the second series of data ports.

In yet another aspect of an electrical device, the first predetermined number of data ports is equal to the second predetermined number of data ports.

A video camera system is also provided. In one aspect of the video camera system, the video camera system includes an electrical device for transmitting and receiving data. The electrical device includes electrical components for receiving, transmitting and processing the data. The electrical components are further configured to facilitate the transmission of power.

The electrical device includes a housing for accommodating the electrical components. The housing includes a panel. The panel includes an interface. The interface includes a plurality of data ports, a first power port and a second power port. The plurality of data ports is disposed between the first power port and the second power port.

The video system further includes a connector kit. The connector kit includes a plurality of connectors. Each of the plurality of connectors includes a power receiving port and a plurality of connection ports. One of the plurality of connectors includes a plurality of connection ports equal in number to the plurality of data ports. A pair of the plurality of connectors is adapted to engage the interface in a manner wherein one of the pair of the plurality of connectors engages the first power port and the other of the pair of plurality of connectors engages the second power port. Further, each one of the pair of the plurality of connectors engages at least one of the plurality of data ports.

In one aspect of the video system, the plurality of data ports includes a first series of data ports and a second series of data ports. The first series of data ports includes a first predetermined number of data ports and the second series of data ports includes a second predetermined number of data ports. The data ports of the first series of data ports are arranged along a common axis. Likewise, the data ports of the second series of data ports are arranged along a common axis.

In another aspect of the video system, the first power port and the second power port are configured to transmit power wirelessly. In such an aspect, the plurality of data ports is configured to transmit the data wirelessly.

In yet another aspect of the video system, the video system further includes a first pair of alignment members and a second pair of alignment members disposed on the interface. In such an aspect, each of the connectors in the plurality of connectors includes one of a third pair of alignment members and a fourth pair of alignment members. The third pair of alignment members is configured to engage the first pair of alignment members and the fourth pair of alignment members is configured to engage the second pair of alignment members.

In yet another aspect of the video system, one of the first pair of alignment members is centered within the first power port and one of the second pair of alignment members is centered within the second power port. In such an aspect, the first series of data ports includes a first uplink port configured to transmit data and the second series of data ports includes a second uplink port configured to transmit data.

In yet another aspect of the video system, the first uplink port is the first data port in the first series of data ports and the second uplink port is the last data port in the second series of data ports.

In yet another aspect of the video system, the first predetermined number of data ports is equal to the second predetermined number of data ports.

In yet another aspect of the video system, the first power port and the first series of data ports collectively define a first connection unit and the second power port, and the second series of data ports collectively define a second connection unit. In such an aspect the video system further includes a first pair of alignment members and a second pair of alignment members. The first pair of alignment members is disposed in the first connection unit and the second pair of alignment members is disposed in the second connection unit. One of the pair of first alignment members is disposed within the first power port and the other of the pair of first alignment members is disposed outside of the first power port in a first direction. In such an aspect, one of the pair of second alignment members is disposed within the second power port and the other of the pair of second alignment members is disposed outside of the second power port in a second direction. The second direction is opposite of the first direction.

BRIEF DESCRIPTION OF THE DRAWINGS

The embodiments set forth in the drawings are illustrative and exemplary in nature and not intended to limit the subject matter defined by the claims. The following description of the illustrative embodiments can be understood when read in conjunction with the following drawings, where like structure is indicated with like reference numerals and in which:

FIG. 4A is a perspective view of a first auxiliary device;

FIG. 4B is a perspective view of a second auxiliary device;

FIG. 6 is a view showing a first auxiliary device and a second auxiliary device mounted to the interface of the electrical device;

DETAILED DESCRIPTION

In one aspect of the disclosure, an electrical device and a video camera system for transmitting and receiving data to at least one auxiliary device is provided. The electrical device includes electrical components for receiving, transmitting and processing the data. The electrical components are further configured to transmit power. The electrical device includes a housing for accommodating the electrical components. The housing includes a panel. The panel includes an interface. The interface includes a plurality of data ports, a first power port and a second power port. The plurality of data ports is disposed between the first power port and the second power port. The interface is configured to mate with a plurality of connectors, each of which are coupled to the auxiliary device so as to power the respective auxiliary device and transmit and receive data to and from the auxiliary device. Accordingly, the electrical device and the video system are configured to accommodate a plurality of different auxiliary components without increasing the space for interfaces, relative to the prior art.

Figure 1:
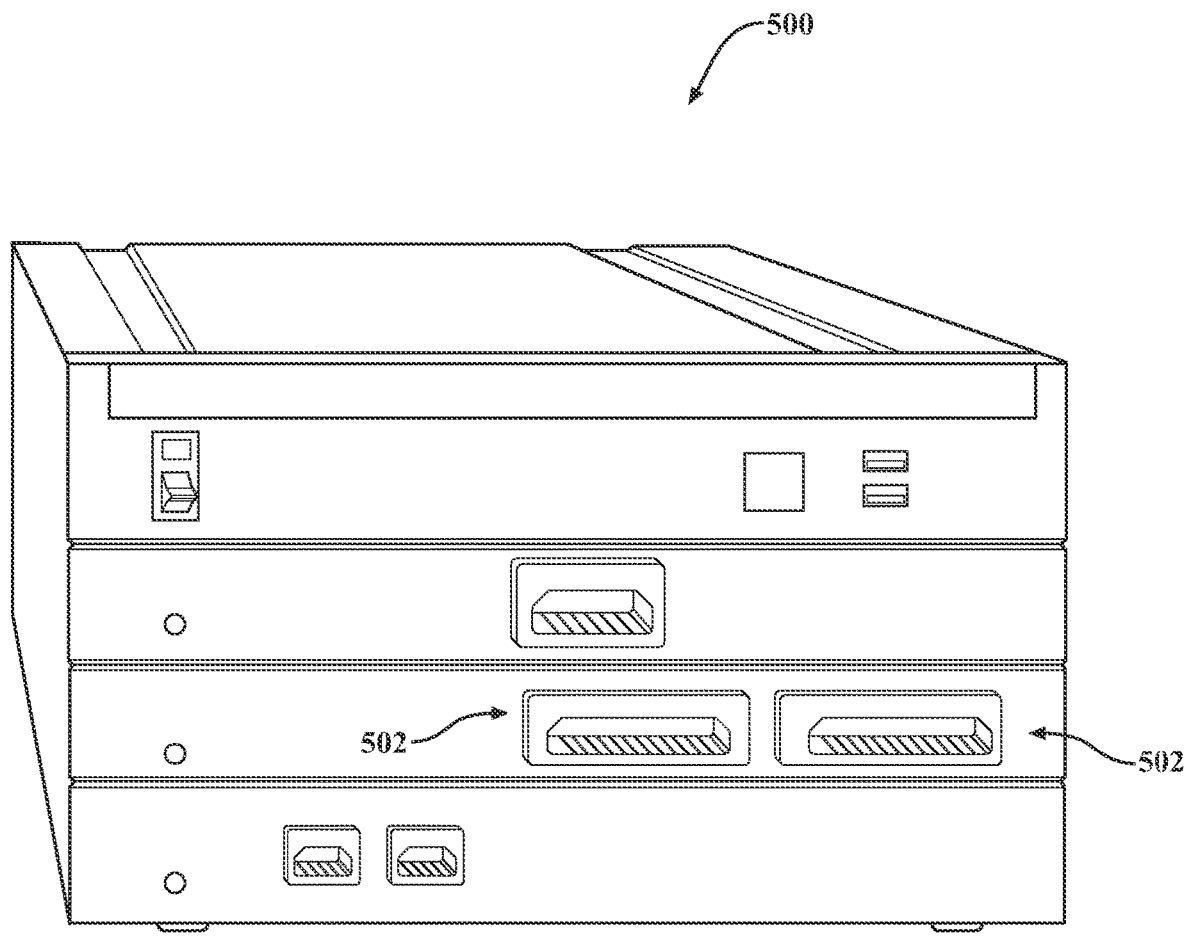
FIG. 1 is a perspective view of a conventional electrical device.
Figure 2:
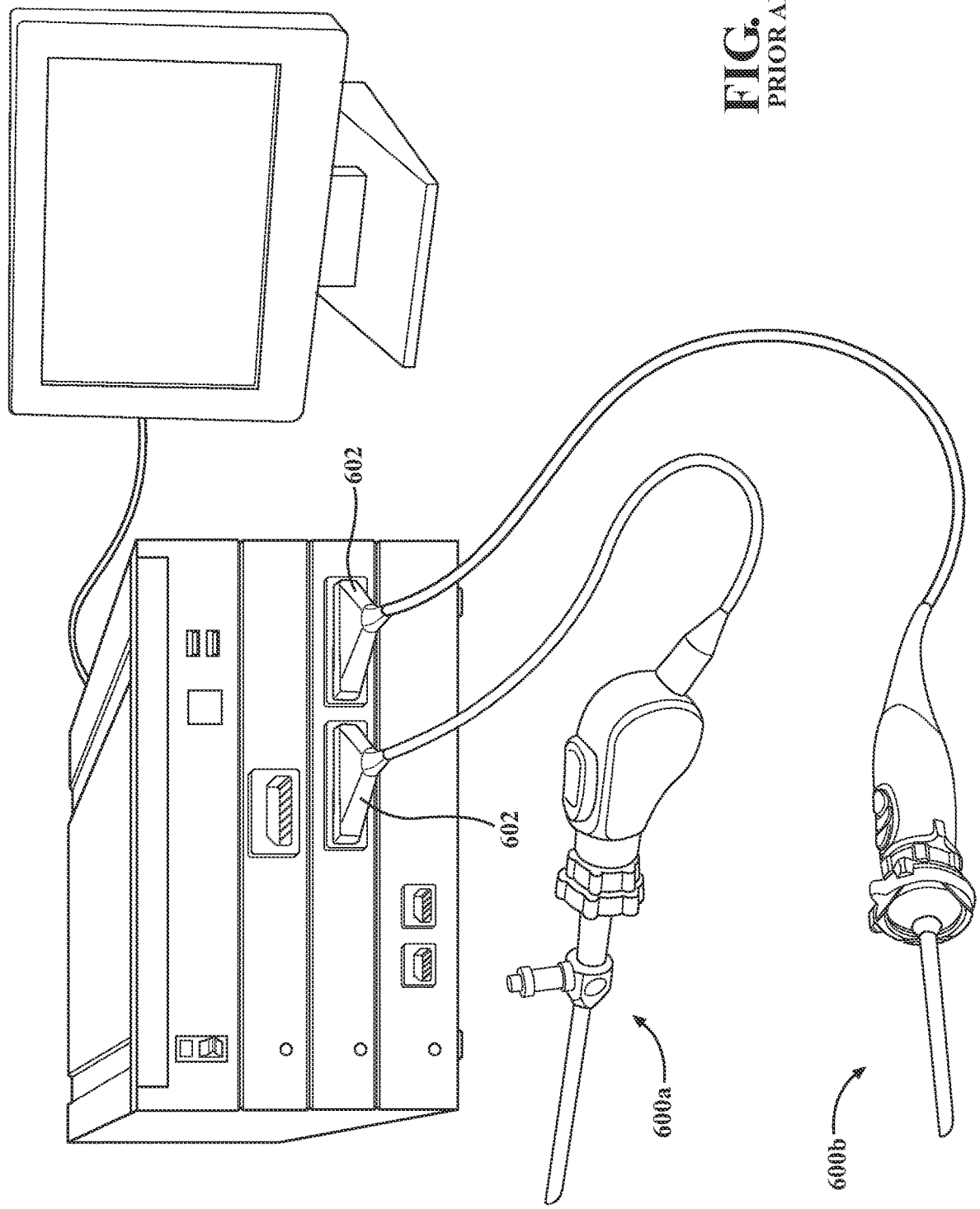
FIG. 2 is a perspective view of the conventional electrical shown in FIG. 1 with a pair of conventional connectors attached thereto.
Figure 3A:
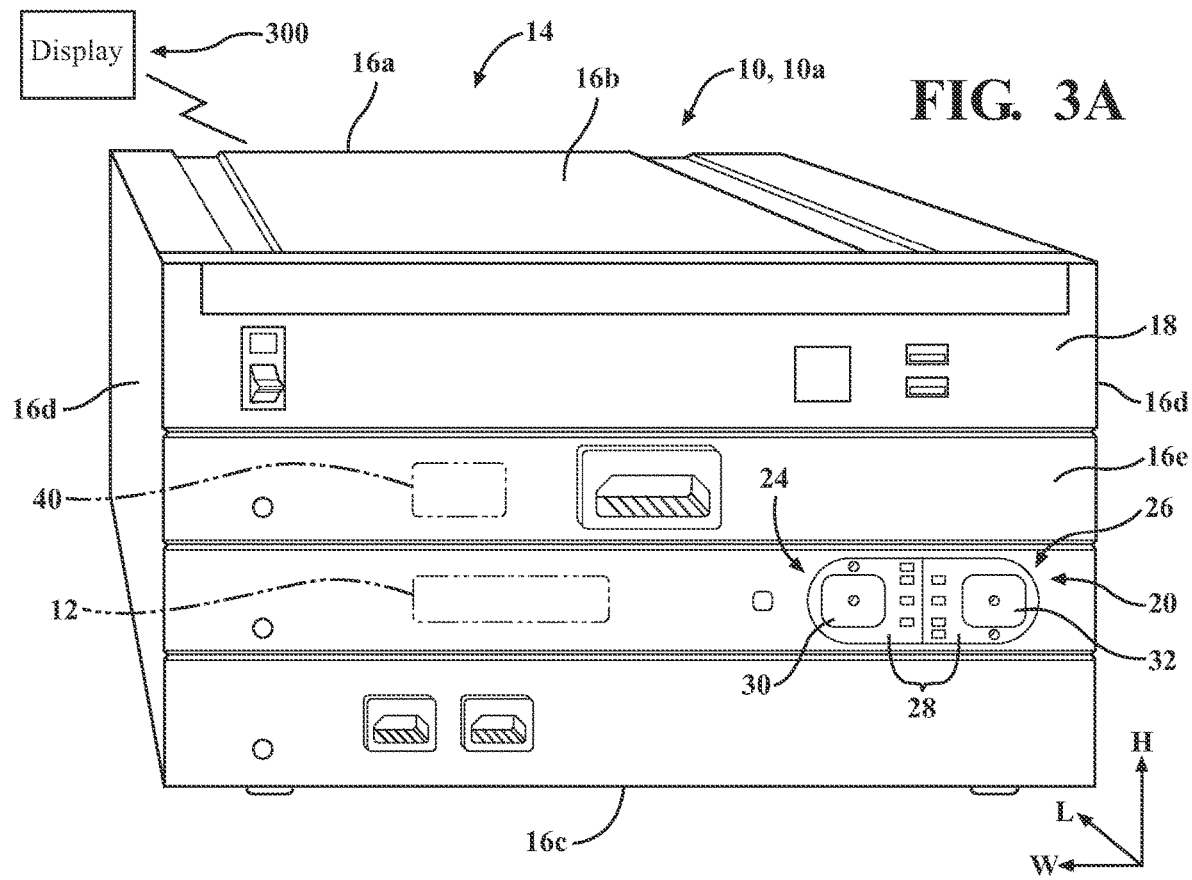
FIG. 3A is a perspective view of an electrical device according to one or more aspects described herein.

With reference first to FIG. 3A, an exemplary depiction of an electrical device 10 is provided. For illustrative purposes, the electrical device 10 will be described in the context of a camera control unit 10a. The camera control unit 10a includes a plurality of electrical components 12 for receiving, transmitting and processing data. The camera control unit 10a may be powered directly from a standard residential or commercial outlet. Alternatively, or in addition to, being powered from a standard residential or commercial outlet, the camera control unit 10a may include a battery (not shown) configured to provide power for the operation of the camera control unit 10a and other auxiliary devices 34 vis-a-vis a connector 22. The electrical components 12 may be further configured to facilitate the transmission of power. Any such electrical components 12 include a combination of semiconductor switches, relays, fuses, capacitors and the like mounted onto a printed circuit board; any such electrical components 12 currently known or used may be adapted for use herein. Accordingly, the electrical components 12 are represented generically by a box shown in dashed lines.

The camera control unit 10a includes a housing 14. The housing 14 includes a front panel 16a, a top panel 16b, a bottom panel 16c, a pair of side panels 16d and a back panel 16e. The front panel 16a, the top panel 16b, the bottom panel 16c, the pair of side panels 16d and the back panel 16e are connected together to define a storage space 18 for accommodating the electrical components 12.

The camera control unit 10a further includes an interface 20. For illustrative purposes the interface 20 is shown disposed on the front panel 16a. However, it should be appreciated that the interface 20 may be disposed on any one of the front panel 16a, the top panel 16b, the bottom panel 16c, and the side panels 16d. In particular, the interface 20 is illustratively disposed on the outer surface of the back panel 16e. The interface 20 may be configured to be substantially flush with the outer surface of the back panel 16e. The interface 20 is configured to accommodate at least two connectors 22 (shown in at least FIGS. 4A, 4B) simultaneously.

The interface 20 is defined by a first portion 24 and a second portion 26, which are arranged in a side-by-side relationship. Preferably, the first portion 24 is symmetrical to the second portion 26, that is the shape of the first portion 24 is generally rectangular with a rounded end and likewise the shape of the second portion 26 is generally rectangular with a rounded end; however, the components therein are not necessarily symmetrical to each other. The interface 20 includes a plurality of data ports 28, a first power port 30, and a second power port 32. The first power port 30 is disposed within the first portion 24 of the interface 20 and the second power port 32 is disposed within the second portion 26 of the interface 20.

The data ports 28 are equally distributed between the first portion 24 and the second portion 26 of the interface 20, and are electrically coupled to the electrical components 12. The data ports 28 are configured to receive and transmit data to and from the connectors 22 coupled to the interface 20. The connectors 22 are attached to a respective auxiliary device 34. The connectors 22 include a mating portion 36 adapted to mate with at least a portion of the interface 20. The mating portion 36 is attached to one end of a cable 38, either an electrically conductive wire or a fiber optic wire, as will be explained in greater detail below. Preferably, an auxiliary device 34 is fixedly coupled to the other end of the cable 38.

With reference now to FIGS. 4A and 4B, in the context of a camera control unit 10a, the auxiliary device 34 may be one of a plurality of videoscopes, such as a video endoscope, an exoscope, a camera head, or the like. The auxiliary devices 34 are electrically coupled to a respective connector 22. The auxiliary device 34 is configured to capture video images. The auxiliary device 34 may be further configured to perform various camera functions. As used herein, the term "camera functions" means any function which can adjust a video image to include but not limited to autofocusing, zooming, camera angle changes, video display changes and the like.

Upon connection of data ports 28 with a connector 22, the camera control unit 10a is configured to provide power to, send commands to, and process data from the corresponding auxiliary device 34. The data ports 28 are configured to receive and transmit data between the camera control unit 10a and the attached auxiliary device 34. The data is processed by the electrical components 12 so as to configure the data to be in a format which may be read by a computer processing unit ("CPU") 40. In the aspect of a camera control unit 10a, the CPU 40 processes the data received from the attached auxiliary device 34 to generate video images onto a display unit 42, such as a monitor or a television which is coupled to the camera control unit 10a wirelessly or wired. As it is known, the amount of data transmitted from the auxiliary device 34 to the camera control unit 10a will vary depending on the resolution, frame rate, color gamut, metadata, etc. of the auxiliary device 34. For instance a larger rate of data is transmitted to the camera control unit 10a from an auxiliary device 34 configured to generate a high definition video, such as 4K Ultra-High Definition relative to an auxiliary device 34 configured to generate a standard definition video. The data ports 28 may be further configured to receive command data from the attached auxiliary device 34 to perform one of the various camera functions described above or to provide command data from the camera control unit 10a to the auxiliary device 34.

As stated above, the data ports 28 may be further configured to transmit data through the data ports 28 to control the various camera functions of the video image such as an auto-focus, camera angle, zoom or the like. In such an aspect, inputs 44 may be disposed on the housing 14 to select one of the various camera functions. The user may simply actuate any one of the inputs 44 to select a desired camera function.

Figure 5A:
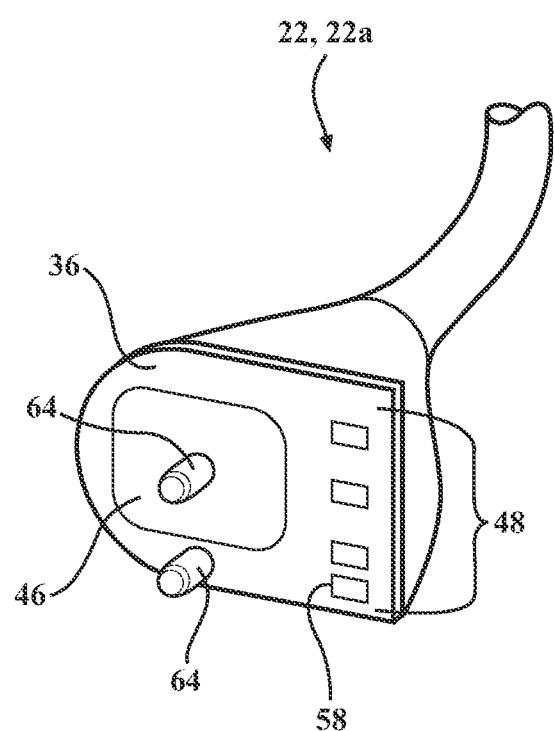
FIG. 5A is a view of the connection port of the connector shown in FIG. 4A.
Figure 5B:
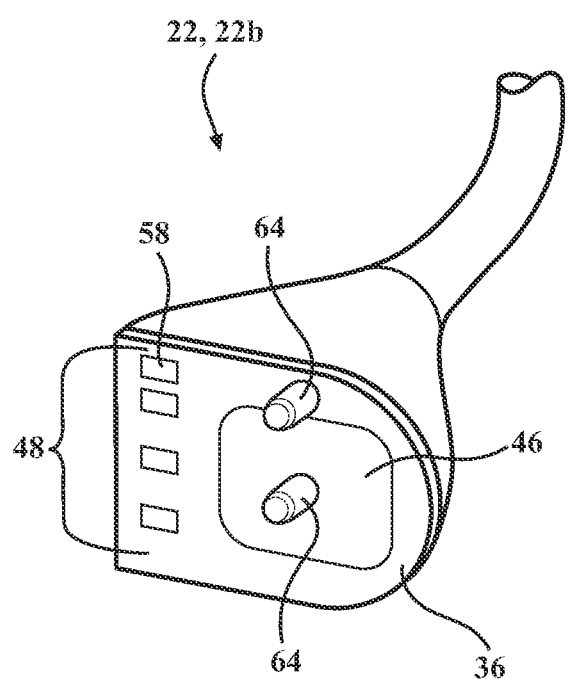
FIG. 5B is a view of the connection port of the connector shown in FIG. 4B.

With reference now to FIGS. 5A and 5B, the mating portion 36 of the connector 22 includes a power receiving port 46 and a plurality of connection ports 48. The connection ports 48 are configured to connect with a corresponding data port 28 of the interface 20 using a coupling means. Any known coupling means may be adapted for use herein, illustratively including a wired connection, such as an electrical wire or a fiber optic connection such as an f-light optical connector. For illustrative purposes FIGS. 3A-12 depict the coupling means as being an optical connection and FIG. 13 depicts the coupling means as being an electrical prong. Naturally, the data ports 28 are configured to receive the respective connection ports 48. It may be that it is desirable to have the coupling means be a combination of various connection means.

Figure 3B:
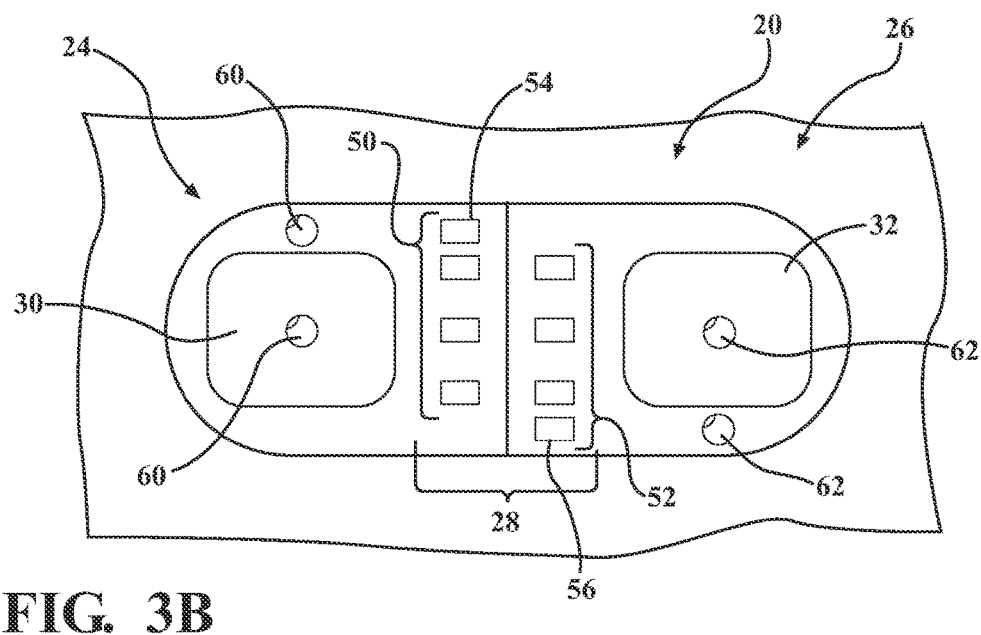
FIG. 3B is a close up view of the interface shown in FIG. 3A.

With reference now to FIG. 3B, the plurality of data ports 28 includes a first series of data ports 50 and a second series of data ports 52. The first series of data ports 50 are arranged in a side-by-side relationship with the second series of data ports 52. The first series of data ports 50 includes a first predetermined number of data ports 28. For illustrative purposes, the first predetermined number of data ports 28 is four (4). The second series of data ports 52 includes a second predetermined number of data ports 28. For illustrative purposes, the second predetermined number of data ports 28 is four (4).

The data ports 28 of the first series of data ports 50 are arranged in line with respect to each other. Likewise, the data ports 28 of the second series of data ports 52 are arranged in line with respect to each other. That is, the first series of data ports 50 and the second series of data ports 52 are each centered along a common vertical axis which extends along a height "H" of the interface 20. It should be appreciated that the number of data ports 28 in the first series of data ports 50 and the second series of data ports 52 is depicted in an illustrative manner and the number of data ports 28 may differ without deviating from the scope of the appended claims. However, it is preferred that the first predetermined number of data ports 28 is equal to the second predetermined number of data ports 28 so as to provide for a symmetry of the interface 20 with respect to the first portion 24 and the second portion 26 of the interface 20. Further, it is preferably that the number of data ports 28 should include at least two (2) in each of the respective first portion 24 and second portion 26 of the interface 20.

In a preferred aspect, the first series of data ports 50 includes a first uplink port 54 configured to transmit data and the second series of data ports 52 includes second uplink port 56 configured to transmit data. In such an aspect, the first uplink port 54 is the first data port 28 in the first series of data ports 50 and the second uplink port 56 is the last data port 28 in the second series of data ports 52. That is, the first uplink port 54 is the first data port 28 in a direction along a height H of the interface 20 extending from the top panel 16b to the bottom panel 16c (i.e., closest to the top panel 16b). Likewise, the second uplink port 56 is the last data port 28 in the second series of data ports 52 in a direction along a height "H" of the interface 20 extending from the top of panel to the bottom panel 16c (i.e., closest to the bottom panel 16c). The uplink ports 54, 56 may provide communication from the camera control unit 10a to adjust parameters of the respective devices 34a, 34b.

The connection ports 48 of the connectors 22 are arranged in line with respect to each other along an axis. One of the connection ports 48 is a receiver port 58 configured to engage a corresponding first uplink port 54 and second uplink port 56. In instances where the connector 22 is configured to engage the first portion 24 of the interface 20, the receive port 58 is configured to engage the first uplink port 54. In instances where the connector 22 is configured to engage the second portion 26 of the interface 20, the receive port 58 is configured to engage the second uplink port 56. The receive port 58 is configured to receive command data from the camera control unit 10a. The command data is processed by the auxiliary device 34 to perform a camera function related to the command data, e.g. zoom, change camera angle, switch the video display.

As stated above, the first power port 30 and the second power port 32 are configured to transmit power so as to power the auxiliary device 34. In one aspect, the first power port 30 and the second power port 32 are configured to transmit power wirelessly using known wireless power transmission methods such as inductive power transfer. Alternatively, the first power port 30 and the second power port 32 are configured to transmit power through a wired connection. Likewise, the plurality of data ports 28 may be configured to transmit the data wirelessly. That is the data may be transmitted in a light medium through a fiber optic cable/wire. Any known method for transmitting data in a light medium, such as infrared light, and the like may be adapted for use herein. The first power port 30 is disposed on one end of the interface 20 and the second power port 32 is disposed on the other end of the interface 20 with the data ports 28 disposed between the first power port 30 and the second power port 32.

The interface 20 may be further configured to align the connector 22 with the interface 20. In such an aspect, the interface 20 includes a pair of first alignment members 60 and a pair of second alignment members 62. The pair of first alignment members 60 and the pair of second alignment members 62 are configured to position the connector 22 so as to register each of the data ports 28 with a corresponding connection port 48, and the first power port 30 or the second power port 32, as the case may be, with a corresponding power receiving port 46 of the connector 22. In such an aspect, one of the pair of first alignment members 60 is centered within the first power port 30 and one of the pair of second alignment members 62 is centered within the second power port 32. The connectors 22 includes a pair of third alignment members 64 which are positioned so as to register with the pair of first alignment members 60 and the pair of second alignment members 62 as the case may be. It is anticipated that the first alignment member 60 and the second alignment 62 shown centered within the respective first and second power ports 30, 32 may be removed wherein the remaining first alignment member 60 and the second alignment member 62 disposed outside of the first and second power ports 30, 32 are aligned horizontally with a respective first and second uplink ports 54, 56.

As shown in FIGS. 3A-13, the pair of first alignment members 60 and the pair of second alignment members 62 are dimples or pin holes disposed on the respective first portion 24 and second portion 26 of the interface 20. The pair of third alignment members 64 are pins which extend outwardly from the mating portion 36 of the connector 22. The third alignment members 64 are dimensioned to generate a pinch fit engagement with the first alignment members 60 and the second alignment members 62, as the case may be.

With continued reference to FIGS. 3A-12, the mating portion 36 of the connectors 22 have connection ports 48 which are adapted to mate with corresponding data ports 28 of the interface 20 so as to provide for a wireless transmission of data. As used herein, the term "mate" means that the connection ports 48 are registered with a corresponding data port 28 so as to facilitate a transfer of data. In particular, the connection ports 48 are the open end of a fiber optic cable. Likewise, the data ports 28 are open ends of a fiber optic cable. Data is carried over light waves and so as to be transferred wirelessly through the fiber optic cable from the auxiliary device 34 to the camera control unit 10a. The engagement of the third alignment members 64 with the respective first alignment members 60 and second alignment members 62 position the connector ports 48 with a corresponding data port 28.

With reference now to FIG. 13, the connection ports 48' are illustratively shown as being male terminal blades. The male terminal blades are configured to be seated within corresponding data ports 28 of the interface 20, wherein the data ports 28 are female terminals configured to receive the male terminal blades of the connector 22g. Such coupling means are currently known and used, and any such coupling means known or later developed may be modified for use herein.

With reference to FIG. 6, a video camera system 100 is also provided. In one aspect of the video camera system 100, the video camera system 100 includes the camera control unit 10a. The camera control unit 10a is configured to transmit and receive data. The camera control unit 10a includes electrical components 12 for receiving, transmitting and processing the data. The electrical components 12 are further configured to facilitate the transmission of power.

The camera control unit 10a includes a housing 14 for accommodating the electrical components 12. The housing 14 includes a back panel 16e. The back panel 16e includes an interface 20. The interface 20 includes a first portion 24 and a second portion 26. The interface 20 further includes a plurality of data ports 28, a first power port 30 and a second power port 32. The first power port 30 is disposed within the first portion 24 of the interface 20 and the second power port 32 is disposed in the second portion 26 of the interface 20. The plurality of data ports 28 are disposed between the first power port 30 and the second power port 32. In a preferred aspect, the plurality of data ports 28 are equally divided between the first portion 24 and the second portion 26 of the interface 20.

The video camera system 100 further includes a connector kit 200, as indicated in FIG. 6. The connector kit 200 includes a plurality of connectors 22a-22f. Each of the connectors 22a-22f are attached to a corresponding auxiliary device 34a-34f. Each of the auxiliary devices 34a-34f is different from one another. While 34c-34f are not shown, it should be understood that each of the auxiliary devices 34a-34f represent a different type of auxiliary device, with each of the different auxiliary devices having different camera capabilities or used for specific surgical functions. For instance one of the auxiliary devices may be an endoscope having 4k resolution, another may be an exoscope having the same or different resolution than the endoscope. Each of the auxiliary devices may be able to perform camera functions such as zoom, angle change, picture capture and the like. In the discussion of the video camera system 100 reference number 22 and 34 may be used to describe the connectors and auxiliary devices generally, and reference number 22 and 34 with alphabetic identifiers are used to describe a specific connector or auxiliary device, as the case may be.

Some of the auxiliary devices 34 may be configured to generate a video image. In particular, such auxiliary devices 34 transmit data, which are processed by the camera control unit 10*a* to generate and display the video image onto a display unit 42. In addition, some of the auxiliary devices 34 include an auxiliary device input 66 which may be operable to change camera functions such as camera angle, zooming, or changing the display to switch between different camera views. For instance, one or more of the auxiliary devices 34 may be configured to generate a white light image and a colored image based upon the fluorescence of a dye. In such an aspect, the auxiliary device input 66 may be configured to change the view on the display unit 42 between a white light image and a colored image.

For illustrative purposes, the connector kit 200 is shown as having six connectors 22*a*, 22*b*, 22*c*, 22*d*, 22*e*, 22*f*. Each of the connectors 22*a*, 22*b*, 22*c*, 22*d*, 22*e*, 22*f* is attached to corresponding auxiliary device 34. Each of the connectors 22*a*, 22*b*, 22*c*, 22*d*, 22*e*, 22*f* includes a power receiving port 46 and a plurality of connection ports 48, including at least one uplink and one downlink port. Each connection port 48 is configured to engage with a corresponding data port 28 so as to transmit and receive data between the camera control unit 10*a* and the connected auxiliary device 34. The power receiving port 46 is configured to couple with one of the first power port 30 or the second power port 32 of the interface 20 so as to be powered by the camera control unit 10*a*. As used herein, the term "couple" means that the power receiving port 46 is connected to the first power port 30 or the second power port 32 to enable a transmission of power from the camera control unit 10*a* to the connected auxiliary device 34.

As disclosed in FIGS. 3A-12, the connector kit 200 includes a plurality of connectors 22*a*, 22*b*, 22*c*, 22*d*, 22*e*, 22*f* further configured to engage the interface 20 in such a manner wherein two auxiliary devices 34 may be attached to the interface 20 simultaneously, or wherein one auxiliary device 34 is attached to all of the data ports 28 of the interface 20 irrespective of the data port 28 being on the first portion 24 or the second portion 26 of the interface 20. In cases where two auxiliary devices 34 are attached simultaneously, as illustrated in at least FIG. 6, each of the auxiliary devices 34 is powered by a respective first and second power ports 30, 32 wherein data from the respective auxiliary devices are transmitted to the camera control unit 10*a* through the respective first and second series of data ports 50, 52 and commands from camera control unit 10*a* are transmitted to the auxiliary devices through the first and second uplink ports 54, 56.

With reference first to FIGS. 3-6, the video system is shown as having a pair of connectors 22*a*, 22*b* adapted to engage the interface 20 in a manner wherein one of the pair of connectors 22*a*, 22*b* engages the first power port 30 and the other of the pair of connectors 22*a*, 22*b* engages the second power port 32. Further each of the connection ports 48 in the first connector 22 and the second connector 22 engages a corresponding one of the data ports 28 of the interface 20. In particular, the receive port 58 of the first connector 22 engages the first uplink port 54 and the connection ports 48 of the first connector 22 engages the first series of data ports 50. Likewise, the receive port 58 of the second connector 22 engages the second uplink port 56 and the connection ports 48 of the second connector engages the second series of data ports 52.

As shown in FIGS. 4A, 4B, and 6, one of the pair of connectors 22*a*, 22*b*, referenced as the first connector 22*a*, is coupled to a first auxiliary device 34*a* and the other of the pair of connectors 22*a*, 22*b*, referenced as the second connector 22*b* is coupled to a second auxiliary device 34*b*. For illustrative purposes, the first auxiliary device 34*a* is shown as being a camera head and the second auxiliary device 34*b* is shown as being a videoscope.

As shown in FIGS. 5A and 5B, the mating portion 36 of the first connector 22*a* and the second connector 22*b* are generally symmetrical to each other. In particular, the connection ports 48 of the first connector 22*a* and the second connector 22*b* are fixed along a line intersecting their respective center points. The mating portion 36 of each of the first connector 22*a* and the second connector 22*b* includes a power receiving port 46 configured to engage the first power port 30 and the second power port 32 respectively. The first connector 22*a* and the second connector 22*b* each include a pair of third alignment members 64 configured to engage with a corresponding pair of alignment members 60, 62 disposed on the first portion 24 of the interface 20.

One of the first alignment members 60 disposed on the first portion 24 of the interface 20 is generally centered within the first power port 30. The other of the first alignment members 60 disposed on the first portion 24 of the interface 20 is disposed outside of the first power port 30 in a first direction so as to be positioned above the first power port 30 when coupled with the interface 20. Likewise, one of the second alignment members 62 disposed on the second portion 26 of the interface 20 is generally centered within the second power port 32 and the other second alignment member 62 is disposed outside of the second power port 32 in a second direction opposite of the first direction so as to be positioned beneath the second power port 32 when coupled with the interface 20. As such, the mating portion 36 of the first connector 22*a* is symmetrical to the mating portion 36 of the second connector 22*b* so as to ensure the first connector 22*a* is mounted to the first portion 24 of the interface 20 and the second connector 22*b* is mounted to the second portion 26 of the interface 20. As shown in FIG. 6, the first connector 22*a* and the second connector 22*b* are mounted to the interface 20 so as to substantially cover the interface 20.

Figure 7:
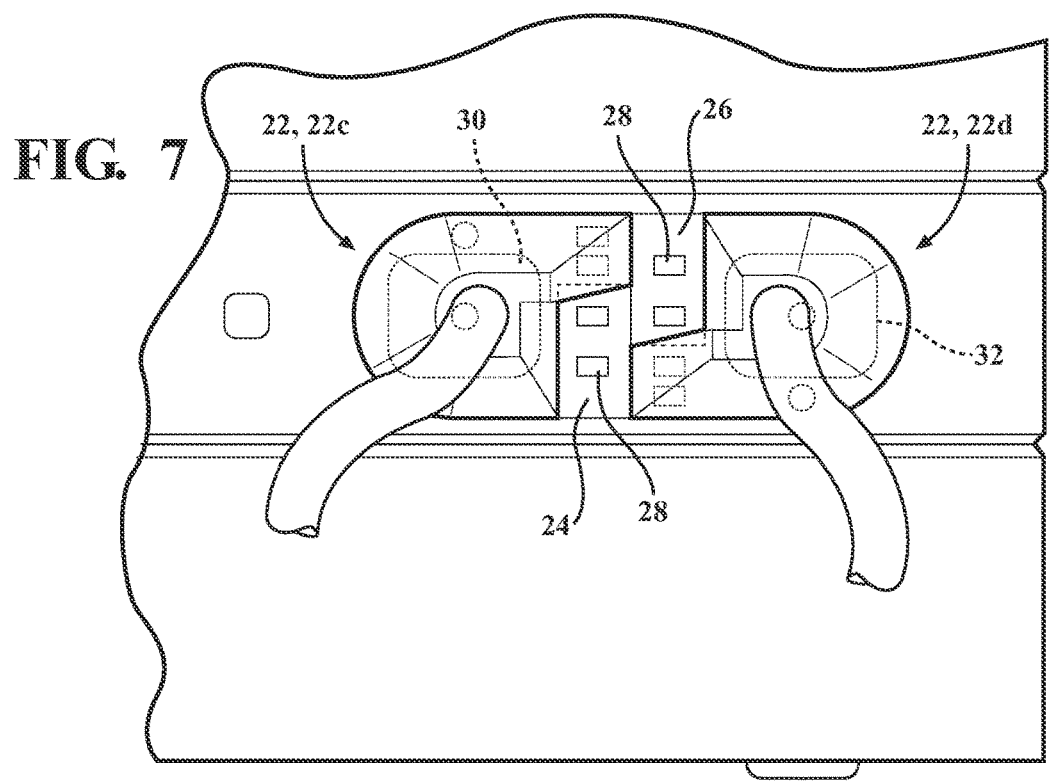
FIG. 7 is a view showing a third auxiliary device and a fourth auxiliary device mounted to the interface of the electrical device.
Figure 8A:
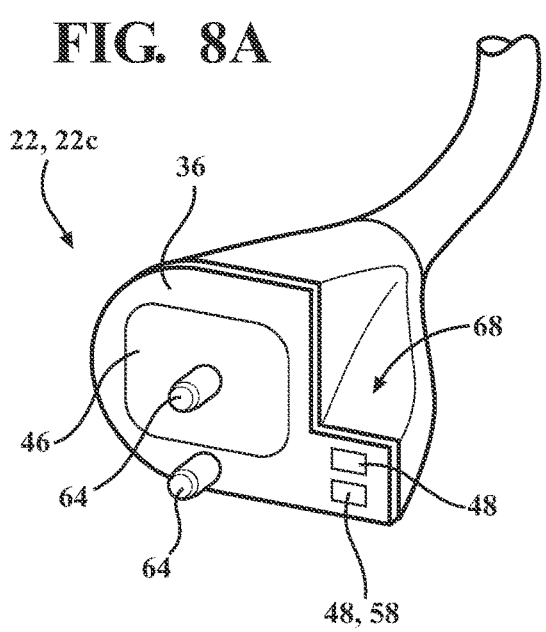
FIG. 8A is a view of the connection port of the third auxiliary device shown in FIG. 7.
Figure 8B:
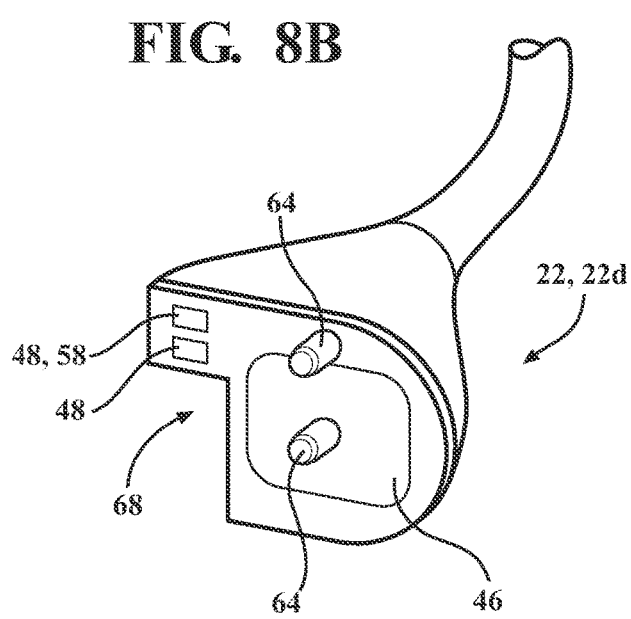
FIG. 8B is a view of the connection port of the fourth auxiliary device shown in FIG. 7.

With reference first to FIGS. 7-8B, the video camera system 100 is shown as being connected to a third connector 22*c* and a fourth connector 22*d*. The third connector 22*c* and the fourth connector 22*d* are attached to a respective third auxiliary device 34*c* (not shown) and a fourth auxiliary device 34*d* (not shown). The third auxiliary device 34*c* and the fourth auxiliary device 34*d* are configured to provide a video image. The third connector 22*c* is configured to engage the first portion 24 of the interface 20 and the fourth connector 22*d* is configured to engage the second portion 26 of the interface 20.

The mating portion 36 of the third connector 22*c* is symmetrical to the mating portion 36 of the fourth connector 22d. As such, the third connector 22c cannot be inserted into the second portion 26 of the interface 20 and the fourth connector 22d cannot be inserted into the first portion 24 of the interface 20 as the third alignment members 64 of the third connector 22c and the fourth connector 22d are not registered with the respective alignment members 60, 62 of the first portion 24 and the second portion 26 of the interface 20.

The third and fourth connectors 22c, 22d have fewer connection ports 48 relative to the first and the second connectors 22a, 22b. The third auxiliary device 34c and the fourth auxiliary device 34d are configured to provide a video image and may be configured to perform camera functions. The video image may be of a lower resolution relative to the first and second auxiliary devices 34 as the mating portion 36 of the third and fourth connectors 22c, 22d include a single connection port 48 and a single receive port 58.

FIGS. 7-8B depict the third connector 22c and the fourth connector 22d engaged with a respective first portion 24 and second portion 26 of the interface 20. For illustrative purposes, the third connector 22c and the fourth connector 22d are shown as having a mating portion 36 which has a cut-out portion 68 configured to expose two of the data ports 28 in the first series of data ports 50 and the second series of data ports 52 respectively. However, it should be appreciated that mating portion 36 of the third connector 22c and the fourth connector 22d may have a shape similar to the mating portion 36 of the first and second connector 22a, 22b. In such an aspect, the third and fourth connectors 22c, 22d cover the interface 20.

Figure 9:
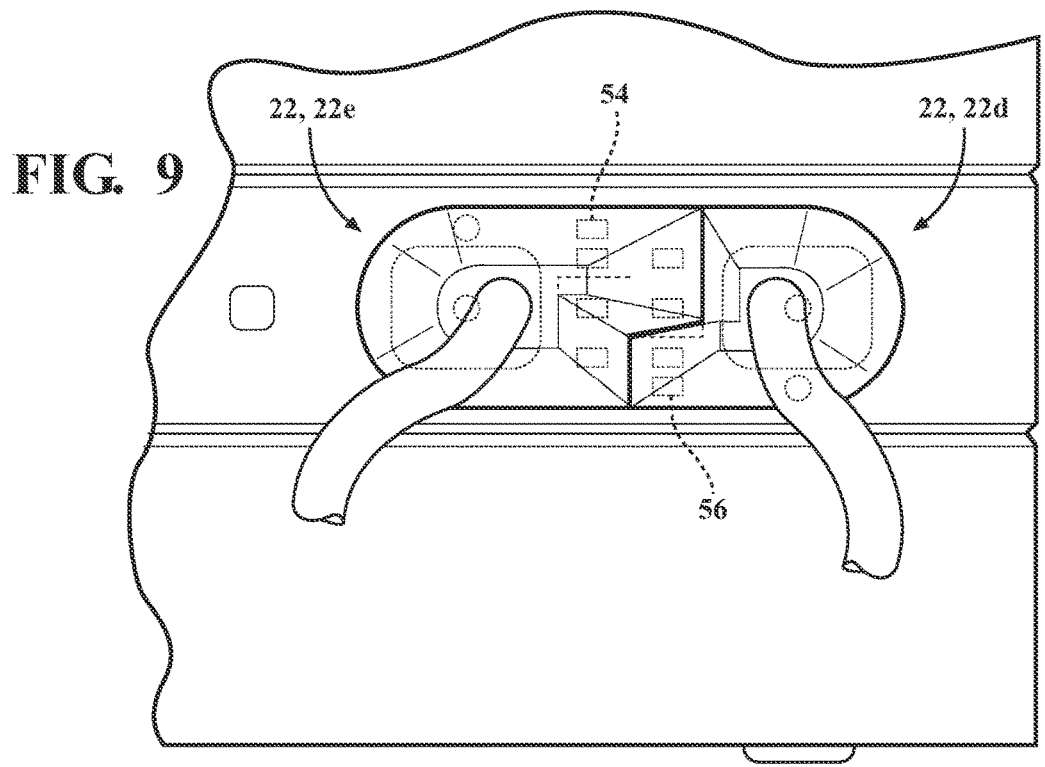
FIG. 9 is a view showing a fifth auxiliary device and a sixth auxiliary device mounted to the interface of the electrical device.
Figure 10A:
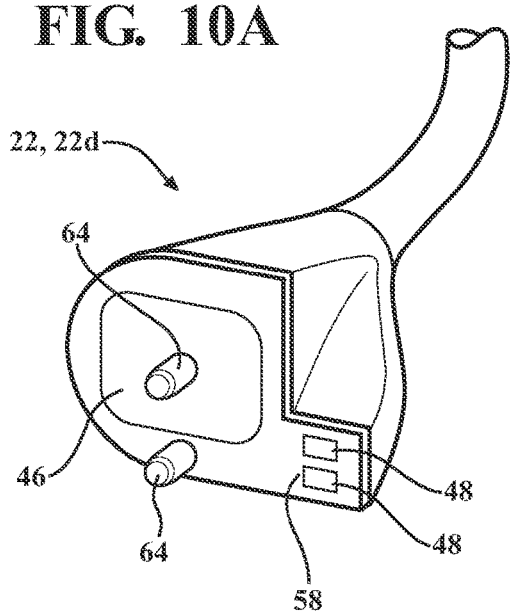
FIG. 10A is a view of the connection port of the fifth auxiliary device shown in FIG. 9.
Figure 10B:
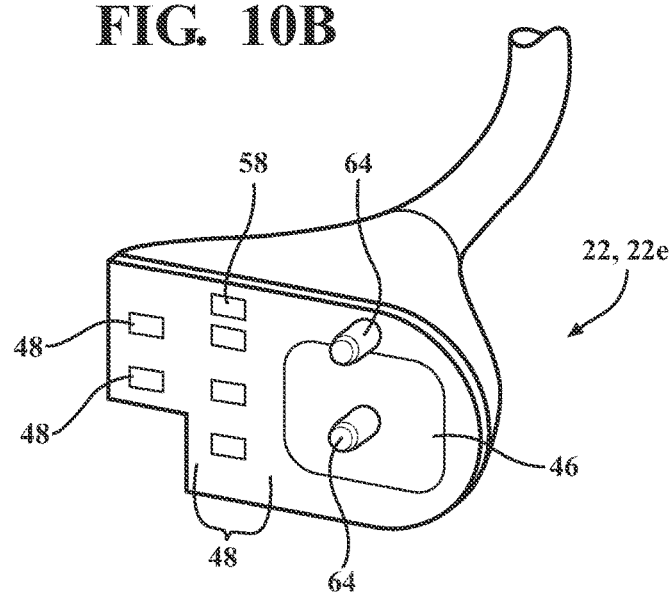
FIG. 10B is a view of the connection port of the sixth auxiliary device shown in FIG. 9.

With reference now to FIGS. 9-10B, the video camera system 100 is shown as being connected to a fifth connector 22e and the fourth connector 22d. The fourth connector is also illustrated in FIGS. 7 and 8B. The fifth connector 22e and the fourth connector 22d are attached to a respective fifth auxiliary device 34e and the fourth auxiliary device 34d (not shown). The fifth auxiliary device 34e and the fourth auxiliary device 34d are configured to provide a video image. The fifth connector 22e is configured to engage the first portion 24 and a portion of the second portion 26 of the interface 20.

The fourth connector 22d is configured to engage the first portion 24 of the interface 20. The mating portion 36 of the fifth connector 22e includes a pair of third alignment members 64, a power receiving port 46 and a plurality of connection ports 48. In particular, the mating portion 36 of the fifth connector 22e includes two (2) columns of connection ports 48. A first column of connection ports 48 includes a number of connection ports 48 equal to the first series of data ports 50 and is configured to be disposed within the first portion 24 of the interface 20.

A second column of connection ports 48 is disposed in parallel with the first column of connection ports 48 and includes two (2) connection ports 48. The second column of connection ports 48 is configured to be disposed within the second portion 26 of the interface 20. As such, the fifth connector 22e cannot be fully inserted into the second portion 26 of the interface 20 and the fourth connector 22d cannot be inserted into the first portion 24 of the interface 20 as the third alignment members 64 of the fifth connector 22e and the fourth connector 22d are not registered with the respective first alignment members 60 and the second alignment members 62 of the first portion 24 and the second portion 26 of the interface 20.

The fifth connector 22e has more connection ports 48 relative to the first, second, third and fourth connectors 22a, 22b, 22c, 22d. The fifth auxiliary device 34e is configured to provide a video image and may be configured to perform camera functions. The video image may be of a higher resolution relative to the first, second, third and fourth auxiliary devices 34 as the mating portion 36 of the fifth connector 22e includes a total of five connection ports 48 and a single receive port 58. Accordingly, more image data may be transmitted from the fifth auxiliary device 34e relative to the first, second, third and fourth auxiliary devices 34.

FIG. 9 depicts the fifth connector 22e and the fourth connector 22d engaged with the interface 20. In this aspect, the interface 20 is fully engaged. The camera control unit 10a is configured to power the fifth auxiliary device 34e and the fourth auxiliary device 34d. The fifth connector 22e and the fourth connector 22d are nested together, so as to be flush against each other and cover the entire interface 20. FIG. 9 illustrates a benefit of the camera control unit 10a. In particular, the camera control unit 10a is configured to power two different auxiliary devices 34 at the same time, wherein each of the auxiliary devices 34 are different and have different camera resolutions.

Figure 11:
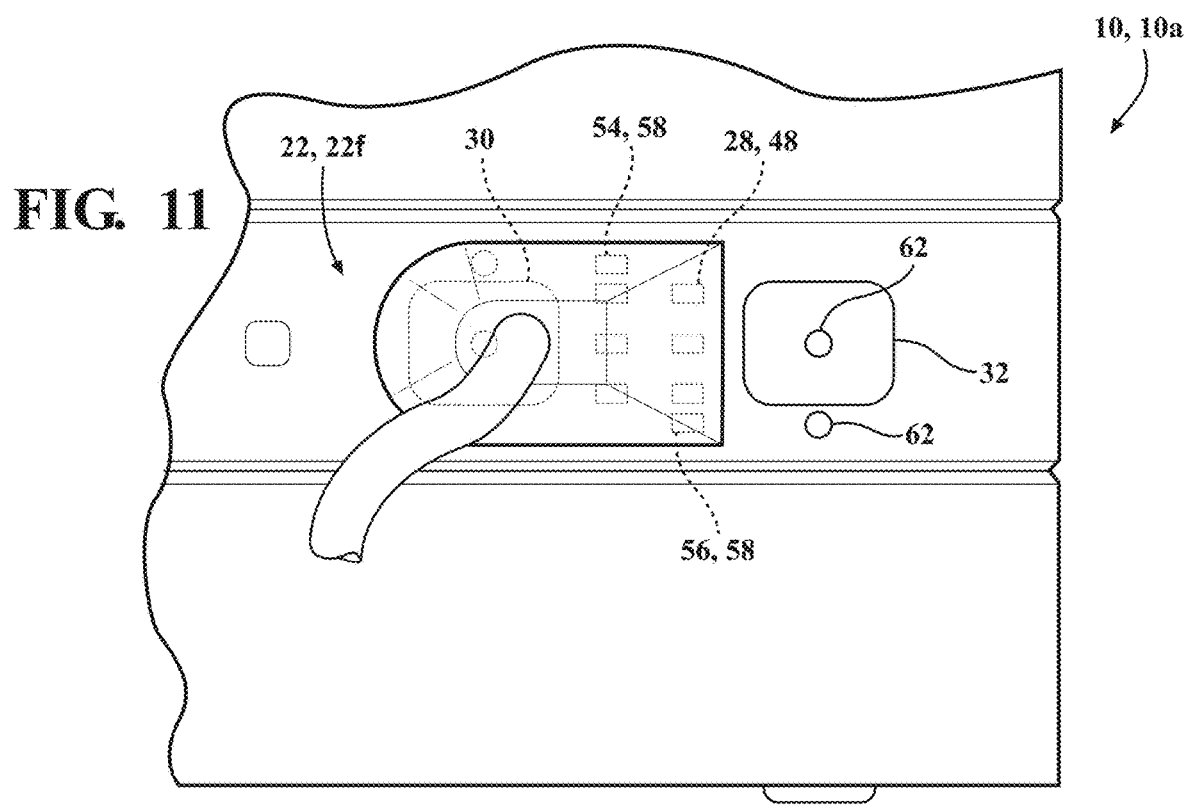
FIG. 11 is a view showing a seventh auxiliary device mounted to the interface of the electrical device.
Figure 12:
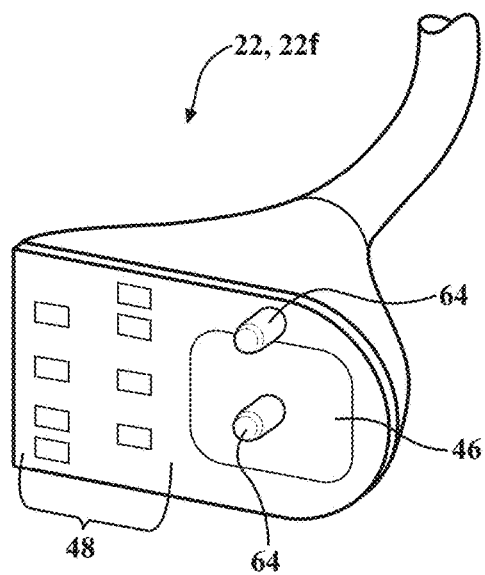
FIG. 12 is a view of the connection port of the seventh auxiliary device shown in FIG. 11.
Figure 13:
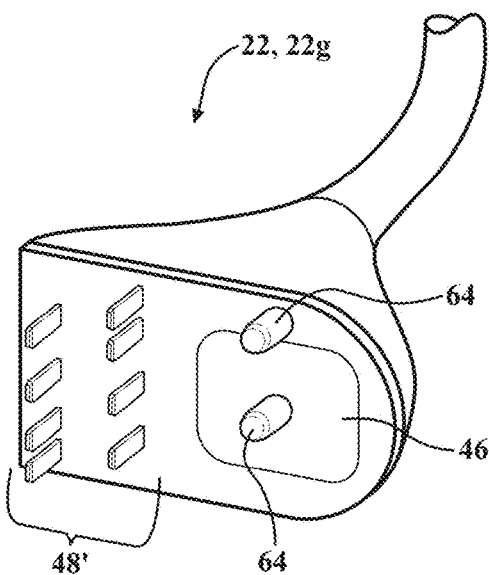
FIG. 13 is an illustrative view of a mating portion of a connector in accordance with a second aspect of the disclosure.

With reference now to FIGS. 11 and 12, the video system is shown as being connected to a sixth connector 22f. The sixth connector 22f is attached to a sixth auxiliary device 34f (not shown). The sixth auxiliary device 34f is configured to provide a video image. The sixth connector 22f is configured to engage the first portion 24 and a portion of the second portion 26 of the interface 20. The mating portion 36 of the sixth connector 22f includes a pair of third alignment members 64, a power receiving port 46 and a plurality of connection ports 48. In particular, the mating portion 36 of the sixth connector 22f includes two (2) columns of connection ports 48. A first column of connection ports 48 includes a number of connection ports 48 equal to the first series of data ports 50 and is configured to be disposed within the first portion 24 of the interface 20.

A second column of connection ports 48 is disposed in parallel with the first column of connection ports 48 and a number of connection ports 48 equal to the second series of data ports 52. The first column of connection ports 48 is offset from the second column of connection ports 48 with respect to a height of the interface 20. In particular, the first column of connection ports 48 is elevated with respect to the second column of connection ports 48 so as to be aligned with the corresponding first series of data ports 50 and the second series of data ports 52. As such, the sixth connector 22f may be configured to engage the either the first power port 30 or the second power port 32.

The sixth connector 22f has more connection ports 48 relative to the first, second, third, fourth and fifth connectors 22a, 22b, 22c, 22d, 22e. The sixth auxiliary device 34f is configured to provide a video image and may be configured to perform camera functions. The video image may be of a higher resolution relative to the first, second, third, fourth and fifth auxiliary devices 34a, 34b, 34c, 34d, 34e as the mating portion 36 of the sixth connector 22f includes a total of six (6) connection ports 48 and two (2) receive ports 58. Accordingly, more image data may be transmitted from the sixth auxiliary device 34f relative to the first, second, third, fourth and fifth auxiliary devices 34a, 34b, 34c, 34d, 34e.

FIG. 11 depicts the sixth connector 22f engaged with the interface 20. In this aspect, second power port 32 is not used. However, due to the arrangement of the connection ports 22 on the mating portion 36 of the connector 22, the sixth connector 22f may be engaged with the second power port 32 in which case the first power port 30 would be exposed. As shown, the sixth connector 22f is configured to engage all of the data ports 28 of the interface 20. Accordingly, auxiliary devices 34 with a high camera resolution, such as 4K High definition may be used.

The electronic device 10 and the video camera system 100 described herein is configured to power two auxiliary devices 34 and also process data from two auxiliary devices 34 simultaneously. More particularly, the electronic device 10 and the video camera system 100 includes an interface 20 which is configured to be used with a connector kit 200 having a plurality of different mating portions 36 configured to selectively engage a predetermined number of data ports 28 of the interface 20 so as to allow for the use of auxiliary devices 34 having different data transmission rates. In one aspect, the auxiliary devices 34 are configured to generate a video image and may provide video images of different resolutions. As such, unlike conventional systems which require a specific interface 20 for a specific auxiliary device 34, the electronic device disclosed herein eliminates the packaging space for engaging the auxiliary devices 34 by utilizing a single interface 20.

For example, the interface 20 may include other layouts with a plurality of power ports (first and second power ports 30,32 and other power ports not shown), a plurality of data ports 28, and alignment members 60 for which three or more connectors 22 may be configured for simultaneous coupling. A tessellated pattern of connectors may be configured to simultaneously engage three or more connectors with three or more power ports while each connector selectively engages at least one of the plurality of data ports disposed between the three power ports.

A number of implementations have been described. Nevertheless, it will be understood that various modifications may be made without departing from the spirit and scope of the disclosure. Accordingly, other implementations are within the scope of the following claims.

I claim:

1. An electrical device for transmitting and receiving data, the electrical device including electrical components for receiving, transmitting and processing the data, the electrical components further configured to transmit power, the electrical device comprising:
a housing for accommodating the electrical components, the housing including a panel, the panel having an interface, the interface including a plurality of data ports and a plurality of power ports, the plurality of power ports including a first power port and a second power port, the plurality of data ports disposed between the first power port and the second power port; and
a first pair of alignment members and a second pair of alignment members, wherein one of the first pair of alignment members is centered within the first power port and wherein one of the second pair of alignment members is centered within the second power port.

2. The electrical device as set forth in claim 1, wherein the plurality of data ports includes a first series of data ports and a second series of data ports, the first series of data ports includes a first predetermined number of data ports arranged along a first common axis and wherein the second series of data ports includes a second predetermined number of data ports that are arranged along a second common axis.

3. The electrical device as set forth in claim 1, wherein the first power port and the second power port are configured to transmit power wirelessly.

4. The electrical device as set forth in claim 1, wherein the plurality of data ports is configured to transmit the data wirelessly.

5. The electrical device as set forth in claim 2, wherein the first series of data ports includes a first uplink port configured to transmit data and wherein the second series of data ports includes a second uplink port configured to transmit data.

6. The electrical device as set forth in claim 5, wherein the first uplink port being the first in the first series of data ports and the second uplink port being the last in the second series of data ports.

7. The electrical device as set forth in claim 2, wherein the first predetermined number of data ports is equal to the second predetermined number of data ports.

8. A video camera system comprising:
an electrical device for transmitting and receiving data, the electrical device including electrical components for receiving, transmitting and processing the data, the electrical components further configured to transmit power, the electrical device including:
a housing for accommodating the electrical components, the housing including a panel, the panel having an interface, the interface including a plurality of data ports and a first power port and a second power port, the plurality of data ports disposed between the first power port and the second power port; and
a connector kit, the connector kit including a plurality of connectors each of the plurality of connectors having a power receiving port and a plurality of connection ports;
wherein one of the plurality of connectors includes a plurality of connection ports equal in number to the plurality of data ports; and
wherein a pair of the plurality of connectors is adapted to engage the interface in a manner wherein one of the pair of the plurality of connectors engages the first power port and the other of the pair of plurality of connectors engages the second power port and wherein each one of the pair of the plurality of connectors engages at least one of the plurality of data ports.

9. The video camera system as set forth in claim 8, wherein the plurality of data ports includes a first series of data ports and a second series of data ports, the first series of data ports includes a first predetermined number of data ports arranged along a common axis and wherein the second series of data ports includes a second predetermined number of data ports.

10. The video camera system as set forth in claim 8, wherein the first power port and the second power port are configured to transmit power wirelessly.

11. The video camera system as set forth in claim 8, wherein the plurality of data ports is configured to transmit the data wirelessly.

12. The electrical device as set forth in claim 8, further including a first pair of alignment members and a second pair of alignment members disposed on the interface, and each of the connectors in the plurality of connectors includes one of a third pair of alignment members and a fourth pair of alignment members, the third pair of alignment members configured to engage the first pair of alignment members and the fourth pair of alignment members is configured to engage the second pair of alignment members.

13. The electrical device as set forth in claim 12, wherein one of the first pair of alignment members is centered within the first power port and wherein one of the second pair of alignment members is centered within the second power port.

14. The electrical device as set forth in claim 8, wherein the first series of data ports includes a first uplink port configured to transmit data and wherein the second series of data ports includes a second uplink port configured to transmit data.

15. The electrical device as set forth in claim 14, wherein the first uplink port being the first in the first series of data ports and the second uplink port being the last in the second series of data ports.

16. The electrical device as set forth in claim 9, wherein the first predetermined number of data ports is equal to the second predetermined number of data ports.

17. The electrical device as set forth in claim 9, wherein the first power port and the first series of data ports define a first connection unit and the second power port, and the second series of data ports define a second connection unit.

18. The electrical device as set forth in claim 17, further including a first pair of alignment members and a second pair of alignment member, the first pair of alignment members disposed in the first connection unit and the second pair of alignment members disposed in the second connection unit, wherein one of the pair of first alignment members is disposed within the first power port and the other of the pair of first alignment members is disposed outside of the first power port in a first direction, and wherein one of the pair of second alignment members is disposed within the second power port and the other of the pair of second alignment members is disposed outside of the second power port in a second direction, the second direction opposite of the first direction.

* * * * *